US009538937B2

(12) United States Patent
Rohde et al.

(10) Patent No.: US 9,538,937 B2
(45) Date of Patent: Jan. 10, 2017

(54) SYSTEM AND METHOD OF EVALUATING A SUBJECT WITH AN INGESTIBLE CAPSULE

(75) Inventors: Bemina L. Rohde, Cheektowaga, NY (US); Christopher D. Bierl, East Aurora, NY (US); Kai-Sing J. Hwang, Orchard Park, NY (US)

(73) Assignee: COVIDIEN LP, Mansfield, MA (US)

( * ) Notice: Subject to any disclaimer, the term of this patent is extended or adjusted under 35 U.S.C. 154(b) by 1117 days.

(21) Appl. No.: 12/456,151

(22) Filed: Jun. 12, 2009

(65) Prior Publication Data

US 2009/0318783 A1    Dec. 24, 2009

Related U.S. Application Data

(60) Provisional application No. 61/132,379, filed on Jun. 18, 2008.

(51) Int. Cl.
*A61B 5/07* (2006.01)
*A61B 5/145* (2006.01)
(Continued)

(52) U.S. Cl.
CPC ........... *A61B 5/073* (2013.01); *A61B 5/14539* (2013.01); *A61B 5/411* (2013.01); *A61B 5/42* (2013.01);
(Continued)

(58) Field of Classification Search
USPC .......................................................... 600/302
See application file for complete search history.

(56) References Cited

U.S. PATENT DOCUMENTS

| 3,683,389 A | 8/1972 | Hollis |
| 3,909,792 A | 9/1975 | Harris |

(Continued)

FOREIGN PATENT DOCUMENTS

| DE | 34 40 177 | 5/1986 |
| EP | 1 618 832 | 1/2006 |

(Continued)

OTHER PUBLICATIONS

Evans et al., Measurement of Gastrointestinal pH Profiles in Normal Ambulant Human Subjects, Gut., Aug. 29, 1988 (8): 1035-1041.

(Continued)

*Primary Examiner* — Navin Natnithithadha
*Assistant Examiner* — Michael R Bloch
(74) *Attorney, Agent, or Firm* — Pearl Cohen Zedek Latzer Baratz LLP

(57) ABSTRACT

A computerized method of analyzing measurements obtained from the gastrointestinal tract of subject comprising the steps of providing an ingestible capsule (20) having a sensor (22, 23, 24) for measuring a parameter of the gastrointestinal tract of a subject, having a subject ingest (118) the capsule, recording (130) measurements from the sensor as the capsule passes through the gastrointestinal tract of the subject, transmitting (131, 122) the measurements to a processor (31), conditioning (132) the measurements to provide data as a function of a time interval, plotting (133) the data on a display (32), providing a query (205, 216, 234), on the display, receiving input (207a or 207b, 218a or 218b, 237a or 237b) from a user in response to the query, setting a marker (50-53) on the plot (40) at a location as a function of the input, and determining (238) a capsule transit time for a selected portion of the gastrointestinal tract as a function of the location of the marker.

66 Claims, 6 Drawing Sheets

(51) Int. Cl.
*A61B 5/00* (2006.01)
*A61B 5/06* (2006.01)

(52) U.S. Cl.
CPC ............ *A61B 5/6861* (2013.01); *A61B 5/0002* (2013.01); *A61B 5/06* (2013.01); *A61B 2562/0247* (2013.01)

(56) References Cited

U.S. PATENT DOCUMENTS

| | | | |
|---|---|---|---|
| 3,971,362 A | 7/1976 | Pope et al. | |
| 4,008,712 A | 2/1977 | Nyboer | |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 4,936,823 A | 6/1990 | Colvin et al. | |
| 4,989,610 A * | 2/1991 | Patton | A61B 5/04365 600/508 |
| 5,050,613 A * | 9/1991 | Newman et al. | 600/483 |
| 5,279,607 A | 1/1994 | Schentag et al. | |
| 5,333,244 A | 7/1994 | Harashima | |
| 5,392,072 A | 2/1995 | Rodriguez et al. | |
| 5,519,828 A | 5/1996 | Rayner | |
| 5,604,531 A | 2/1997 | Iddan et al. | |
| 5,697,384 A | 12/1997 | Miyawaki et al. | |
| 5,740,267 A | 4/1998 | Echerer | |
| 5,749,908 A | 5/1998 | Snell | |
| 5,761,655 A | 6/1998 | Hoffman | |
| 5,819,736 A | 10/1998 | Avny et al. | |
| 5,822,539 A | 10/1998 | Van Hoff | |
| 5,838,313 A | 11/1998 | Hou | |
| 5,920,317 A | 7/1999 | McDonald | |
| 5,924,074 A | 7/1999 | Evans | |
| 5,970,173 A | 10/1999 | Lee et al. | |
| 5,993,378 A | 11/1999 | Lemelson | |
| 6,097,399 A | 8/2000 | Bhatt | |
| 6,124,864 A | 9/2000 | Madden et al. | |
| 6,188,403 B1 | 2/2001 | Sacerdoti | |
| 6,192,266 B1 | 2/2001 | Dupree et al. | |
| 6,222,547 B1 | 4/2001 | Schwuttke | |
| 6,240,312 B1 | 5/2001 | Alfano et al. | |
| 6,335,736 B1 | 1/2002 | Wagner | |
| 6,346,940 B1 | 2/2002 | Fukunaga | |
| 6,389,311 B1 | 5/2002 | Whayne | |
| 6,428,469 B1 | 8/2002 | Iddan | |
| 6,512,953 B2 | 1/2003 | Florio | |
| 6,614,452 B1 | 9/2003 | Cable | |
| 6,632,175 B1 | 10/2003 | Marshall | |
| 6,675,352 B1 | 1/2004 | Osaki | |
| 6,692,430 B2 | 2/2004 | Adler | |
| 6,709,387 B1 | 3/2004 | Glukhovsky | |
| 6,786,406 B1 | 9/2004 | Maningas | |
| 6,901,284 B1 * | 5/2005 | Maki et al. | 600/476 |
| 6,941,166 B2 * | 9/2005 | MacAdam et al. | 600/521 |
| 7,009,634 B2 | 3/2006 | Iddan | |
| 7,119,814 B2 | 10/2006 | Meron | |
| 7,200,253 B2 | 4/2007 | Glukhovsky | |
| 7,215,338 B2 | 5/2007 | Horn | |
| 7,219,034 B2 | 5/2007 | McGee et al. | |
| 7,245,746 B2 | 7/2007 | Bjaerum | |
| 7,636,092 B2 | 12/2009 | Horn | |
| 7,694,320 B1 | 4/2010 | Yeo | |
| 7,805,178 B1 * | 9/2010 | Gat | 600/407 |
| 8,144,152 B2 | 3/2012 | Horn | |
| 8,228,333 B2 | 7/2012 | Horn | |
| 2001/0017649 A1 | 8/2001 | Yaron | |
| 2001/0051766 A1 | 12/2001 | Gazdzinski | |
| 2002/0021828 A1 | 2/2002 | Papier | |
| 2002/0093484 A1 | 7/2002 | Skala et al. | |
| 2002/0103417 A1 | 8/2002 | Gazdzinski | |
| 2002/0107444 A1 | 8/2002 | Adler | |
| 2002/0171669 A1 | 11/2002 | Meron | |
| 2002/0181680 A1 | 12/2002 | Linder et al. | |
| 2002/0186234 A1 | 12/2002 | Van De Streek | |
| 2002/0193669 A1 | 12/2002 | Glukhovsky | |
| 2002/0198439 A1 | 12/2002 | Mizuno | |
| 2003/0063130 A1 | 4/2003 | Barbieri | |
| 2003/0077223 A1 | 4/2003 | Glukhovsky et al. | |
| 2003/0151661 A1 | 8/2003 | Davidson et al. | |
| 2003/0167000 A1 | 9/2003 | Mullick et al. | |
| 2003/0208107 A1 | 11/2003 | Refael | |
| 2004/0054294 A1 * | 3/2004 | Ramseth | 600/509 |
| 2004/0066398 A1 | 4/2004 | Dolimier | |
| 2004/0103000 A1 | 5/2004 | Owurowa et al. | |
| 2004/0152956 A1 | 8/2004 | Korman | |
| 2004/0184639 A1 | 9/2004 | Jackson | |
| 2004/0196287 A1 | 10/2004 | Wong | |
| 2004/0225223 A1 * | 11/2004 | Honda et al. | 600/476 |
| 2004/0249291 A1 | 12/2004 | Honda et al. | |
| 2004/0257620 A1 | 12/2004 | Loce | |
| 2005/0038680 A1 * | 2/2005 | McMahon | 705/3 |
| 2005/0065450 A1 | 3/2005 | Stuebe et al. | |
| 2005/0075551 A1 | 4/2005 | Horn et al. | |
| 2005/0242946 A1 * | 11/2005 | Hubbard et al. | 340/539.12 |
| 2005/0281446 A1 | 12/2005 | Glukhovsky et al. | |
| 2006/0004304 A1 * | 1/2006 | Parks | A61B 5/037 600/593 |
| 2006/0149140 A1 | 7/2006 | Eldridge | |
| 2006/0184039 A1 * | 8/2006 | Avni | A61B 1/041 600/476 |
| 2007/0102502 A1 | 5/2007 | Nguyen | |
| 2007/0127793 A1 * | 6/2007 | Beckett et al. | 382/128 |
| 2008/0064938 A1 | 3/2008 | Semler et al. | |
| 2009/0105694 A1 * | 4/2009 | Boyden | A61B 5/073 604/891.1 |
| 2009/0275850 A1 * | 11/2009 | Mehendale et al. | 600/523 |

FOREIGN PATENT DOCUMENTS

| | | |
|---|---|---|
| JP | 57-45833 | 3/1982 |
| JP | HEI-3-289779 | 12/1991 |
| JP | 4109927 | 4/1992 |
| JP | HEI-4-180736 | 6/1992 |
| JP | 5015515 | 1/1993 |
| JP | 7289504 | 11/1995 |
| JP | 2001 137182 | 5/2001 |
| JP | 2001 224551 | 8/2001 |
| JP | 2001224553 | 8/2001 |
| JP | 2004/321603 | 11/2004 |
| JP | 2004/337596 | 11/2004 |
| WO | WO 92/21307 | 12/1992 |
| WO | WO 98/11816 | 3/1998 |
| WO | WO 00/58967 | 10/2000 |
| WO | WO 01/50941 | 7/2001 |
| WO | WO 01/08548 | 8/2001 |
| WO | WO 01/65995 | 9/2001 |
| WO | WO 02/26103 | 9/2001 |
| WO | WO 02/10223 | 5/2002 |
| WO | WO 02/067593 | 8/2002 |

OTHER PUBLICATIONS

Robots for the future—Shin-ichi, et al., Nov. 29, 2001.
The Radio Pill, Rowlands, et al., British Communications and Electronics, Aug. 1960, pp. 598-601.
Video Camera to "TAKE"—RF System lab, Dec. 25, 2001.
Wellesley company sends body montiors into space—Crum, Apr. 1998.
www.rfnorkia.com—NORIKA3, Dec. 24, 2001.
Wireless transmission of a color television moving image from the stomach using a miniature CCD camera, light source and microwave transmitter. Swain CP, Gong F, Mills TN. Gastrointest Endosc 1997;45:AB40.
BBC News Online—Pill camera to 'broadcast from the gut', Feb. 21, 2000, www.news.bbc.co.uk.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
Frohlich, B.: "Exploring Geo-Scientific Data in Virtual Environments", ACM Proc.Conf. on Vis., Nov. 1999, pp. 169-173, Figs. 4-5.

(56) References Cited

OTHER PUBLICATIONS

Economides, M.J. et al.: "Advances in Production Engineering", Web, Sep. 11, 2003, http://pumpjack.tamu.edu/-valko/CV/ValkoPDF/CanadianInvPaper.pdf.
Nuntius, et al.:"Multimedia Technology, H.264—A New Technology for Video Compression", pp. 1-4.
International Search Report for Application No. PCT/IL04/00906 dated Mar. 1, 2005.
Davidson T, Shreiber R, Jacob H; Multi-viewing of video streams: a new concept for efficient review of capsule endoscopy studies; Gastrointestinal Endoscopy; 2003; vol. 57, No. 5, p. AB164.
Lewis B.S: "The Utility of Capsule Endoscopy in Obscure Gastrointestinal Bleeding" Techniques in Gastrointestinal Endoscopy, vol. 5, No. 3 Jul. 2003, pp. 115-120.
European Search Report for European Application No. 04770577.7 dated Dec. 8, 2006.
European Search Report of European Application No. 10181052.1 dated Dec. 14, 2010.
Office Action of Australian Application No. 2004277001 dated Nov. 6, 2009.
A. Yoshitaka, T. Ishii, M. Hirakawa, T. Ichikawa, Content-based retrieval of video data by the grammar of film, Sep. 1997, 1997 IEEE Symposium on Visual Languages Proceedings, pp. 310-317.
Internet Archive Webshots of Feb. 29, 2000 weather.com, printed on Oct. 21, 2010, http://web.archive.org/web/*/htlp://www.weather.Com, pp. 1-15.

\* cited by examiner

SYSTEM AND METHOD OF EVALUATING A SUBJECT WITH AN INGESTIBLE CAPSULE

CROSS-REFERENCE TO RELATED APPLICATIONS

This application claims the benefit of U.S. Provisional Patent Application No. 61/132,379, filed Jun. 18, 2008. The entire content of such application is incorporated by reference herein.

TECHNICAL FIELD

The present invention relates generally to ingestible capsules and, more particularly, to a system and process for assisting a user in the evaluation of the gastrointestinal tract of a subject with an ingestible capsule.

BACKGROUND ART

Ingestible capsules are well-known in the prior art. Such capsules are generally small pill-like devices that can be ingested or swallowed by a patient. It is known that such capsules may include one or more sensors for determining physiological parameters of the gastrointestinal tract, such as sensors for detecting temperature, pH and pressure.

A number of methods of determining location of an ingestible capsule are known in the prior art. For example, it is known that signal strength or signal triangulation may be used to attempt to determine the location of an ingested capsule. However, the use of an RF signal has a number of disadvantages, including that it generally requires multiple antennas, various tissues may impact the signal differently, and patient movement may skew the results. It is also known that accelerometers may be used to attempt to determine location, but such methods also have disadvantages, such as drift, non-linear progression and rotational inaccuracy.

It is also known that certain physiological parameters may be associated with regions of the gastrointestinal tract. For example, a 1988 article entitled "Measurement of Gastrointestinal pH Profiles in Normal Ambulant Human Subjects" discloses pH measurements recorded by a capsule passing through the gastrointestinal tract. It is known that pH has been correlated with transitions from the stomach to the small bowel (gastric emptying) and from the distal small bowel to the colon (ileo-caecal junction).

U.S. Patent Publication No. US2006/0149140 discloses a software program configured to interpret patient input data, diagnose the patient's condition, and recommend treatment options. U.S. Patent Publication No. US2002/0181680 discloses a data collection and management system for patient-worn medical devices in which data modems are used to provide for remote data collection and management of a wearable cardiac defibrillator monitor.

DISCLOSURE OF THE INVENTION

With parenthetical reference to corresponding parts, portions or surfaces of the disclosed embodiment, merely for the purposes of illustration and not by way of limitation, the present invention provides a computerized method of analyzing measurements obtained from the gastrointestinal tract of subject comprising the steps of providing an ingestible capsule (20) having a sensor (22, 23, 24) for measuring a parameter of the gastrointestinal tract of a subject, having a subject ingest (118) the capsule, recording (130) measurements from the sensor as the capsule passes through the gastrointestinal tract of the subject, transmitting (131, 122) the measurements to a processor (31), conditioning (132) the measurements to provide data as a function of a time interval, plotting (133) the data on a display (32), providing a query (205, 216, 234) on the display, receiving input (207a or 207b, 218a or 218b, 237a or 237b) from a user in response to the query, setting a marker (50-53) on the plot (40) at a location as a function of the input, and determining (238) a capsule transit time for a selected portion of the gastrointestinal tract as a function of the location of the marker.

The sensor may be selected from a group consisting of a pH sensor (22), a pressure sensor (23) and a temperature sensor. The step of transmitting the measurements to a processor may comprise the steps of transmitting the measurements from the capsule to a receiver (17), and downloading the measurements from the receiver to the processor. The step of conditioning the measurements to provide data as a function of a time interval may comprise the steps of screening the measurements to verify that they are valid. The plot may be a graph (40). The step of providing a query may comprise the steps of showing a suggested marker on the plot at a location and seeking confirmation from the user that the suggested marker is at a desired location (205, 216, 234). The input may comprise confirmation by the user that the suggested marker is at the desired location (207a, 218a, 237a). The step of providing a query may comprise the steps of showing a suggested marker on the plot at a location and allowing the user to move the suggested marker by way of an input device 33 communicating with the processor (207b, 218b, 237b). The input may comprise movement of the suggested marker by the user with the input device. The step of providing a query may comprise the step of allowing the user to position a marker at a desired location on the plot with an input device communicating with the processor and the input may comprise placement of the marker by the user with the input device. The data may be plotted in a first color and the marker may be shown on the plot in a second color different from the first color.

The location of the marker on the plot may correspond to an event selected from a group consisting of ingestion (50), gastric emptying (51), colonic entry (52), and body exit (53). The transit time may be selected from a group consisting of gastric emptying time, small bowel transit time, colonic transit time, whole gut transit time, and oral caecal transit time. The transit time may be displayed on the display. The method may further comprise the step of comparing the transit time to a standard transit time and a result of the comparison may be displayed on the display. The method may further comprise the step of comparing the data to a standard, and the standard may be selected from a group consisting of stomach pH, pH rise from stomach to small bowel, pressure in a portion of the gastrointestinal tract, and a temperature fluctuation.

The method may further comprise the steps of recording an event (134) associated with the subject during transit of the capsule, correlating the event with the data (201), and notating the event on the plot (202). The event may be selected from a group consisting of the subject ingesting the capsule, ingesting food, ingesting liquid, experiencing pain, experiencing nausea, experiencing gas, experiencing bloating, exercising, moving actively, vomiting, resting, waking up, and experiencing a bowel movement. The method may further comprise the step of entering a notation or comments associated with the plot (204).

In another aspect, a computer-readable medium is provided having computer-executable instructions for performing a method comprising receiving measurements of a parameter of a gastrointestinal tract of a subject recorded by a sensor on an ingestible capsule ingested by the subject, conditioning the measurements to provide data as a function of a time interval, plotting the data on a display, providing a query on the display, receiving input from a user in response to the query, setting a marker on the plot at a location as a function of the input, and determining a capsule transit time for a selected portion of the gastrointestinal tract as a function of the location of the marker.

In another aspect, a system for analyzing measurements obtained from the gastrointestinal tract of a subject is provided comprising an ingestible capsule having a sensor adapted to record measurements as the capsule passes through at least a portion of a subject's gastrointestinal tract, a receiver adapted to receive the measurements when transmitted from the capsule, a processor adapted to communicate with the receiver, a display in communication with the processor, an input device in communication with the processor, the processor programmed to receive the measurements, condition the measurements to provide data as a function of a time interval, plot the data on the display, provide a query on the display, receive input from the input device in response to the query, set a marker on the plot at a location as a function of the input, and determine a capsule transit time for a selected portion of the gastrointestinal tract as a function of the location of the marker.

Accordingly, the general object is to provide a method for assisting a user in the evaluation of a subject.

Another object is to provide a method for guiding a user in evaluating a subject.

Another object is to provide a system for guiding a user in evaluating a subject.

These and other objects and advantages will become apparent from the foregoing and ongoing written specification, the drawings, and the claims.

DESCRIPTION OF PREFERRED EMBODIMENTS

Figure 1:
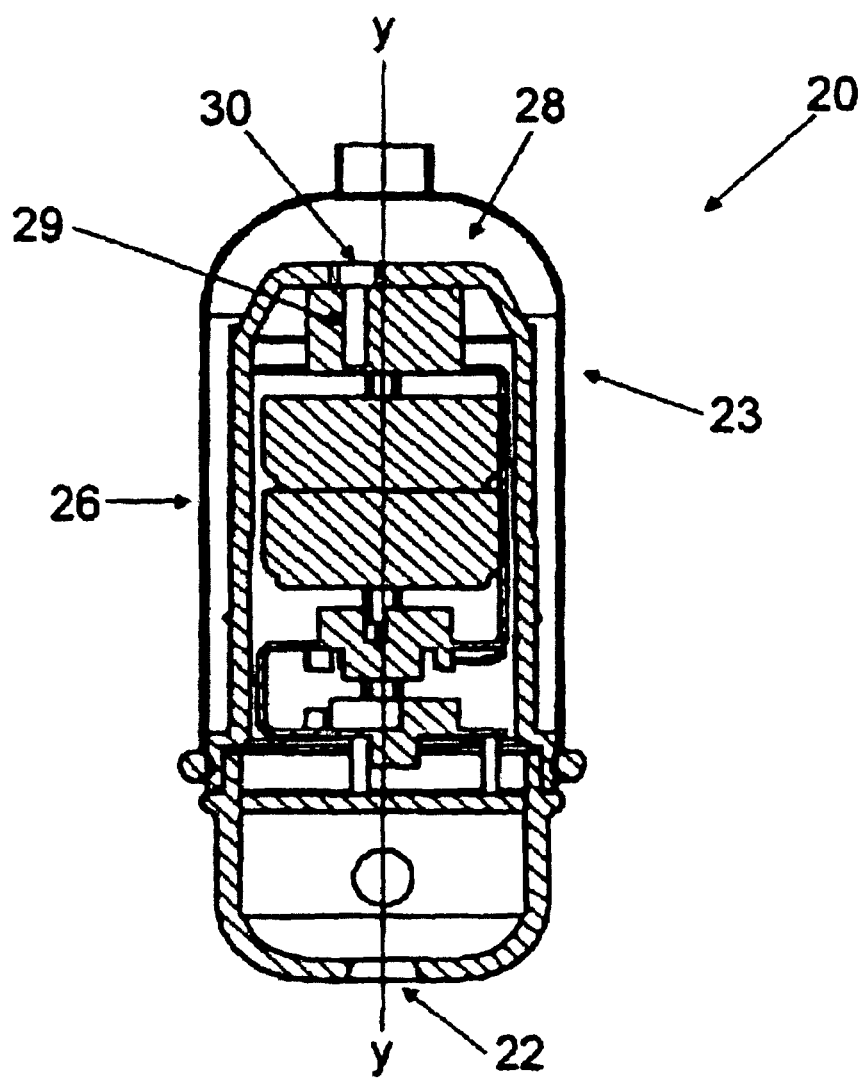
FIG. 1 is a sectional view of an ingestible capsule adapted to record pressure, pH and temperature measurements in a gastrointestinal tract.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 2:
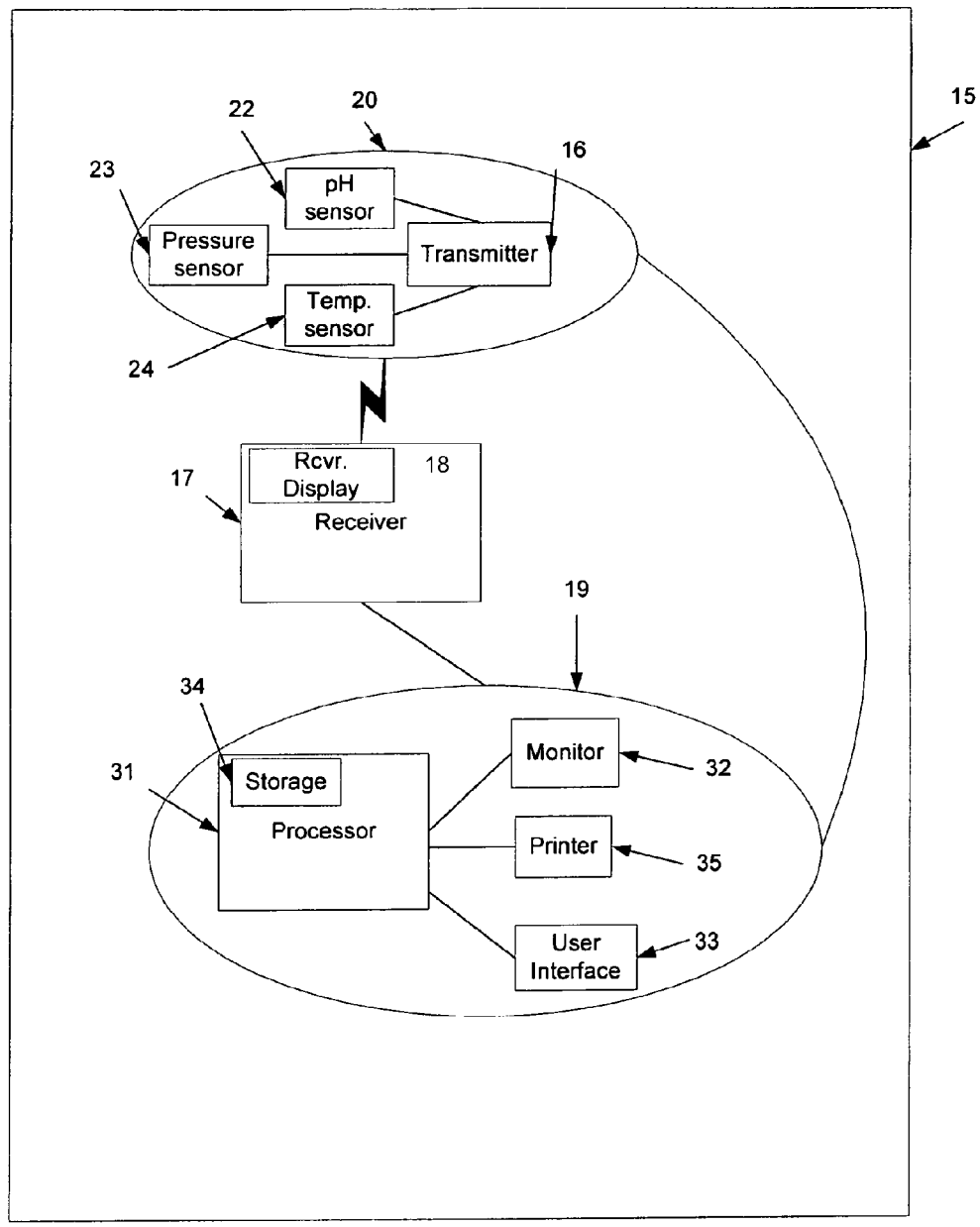
FIG. 2 is a schematic of an embodiment of the improved system.

Referring now to the drawings and, more particularly, to FIG. 2 thereof, this invention provides a new system for evaluating the gastrointestinal tract of a subject with an ingestible capsule, of which the presently preferred embodiment is generally indicated at 15. As shown in FIG. 2, system 15 generally includes an ingestible capsule 20 having a pressure sensor assembly 23 for taking pressure measurements of a subject's gastrointestinal tract, a pH sensor 22 for taking pH measurements of a subject's gastrointestinal tract, and a transmitter 16 for transmitting the measurements, a receiver 17 for receiving signals sent from transmitter 16, and a workstation 19 for processing measurements from sensors 22 and 23.

As shown in FIG. 1, capsule 20 is an elongated ellipsoid-shaped device, somewhat resembling a medicament capsule. The capsule generally has a hard shell or casing which houses the transmitting electronics, battery compartment and sensors. Capsule 20 is adapted to be ingested or otherwise positioned within a tract to sense pressure, pH and temperature within the tract and to transmit such readings. As shown, capsule 20 is generally a cylindrical member elongated about axis y-y and having generally rounded closed ends. The capsule is generally provided with an outer surface to facilitate easy swallowing of the capsule. In the preferred embodiment, capsule 20 is an autonomous swallowable capsule and is self-contained. Thus, capsule 20 does not require any wires or cables to, for example, receive power or transmit information. The pH, pressure and temperature data are transmitted from within the GI tract to data receiver 17.

Capsule 20 includes a pressure sensor assembly 23 comprising a flexible sleeve 26 affixed to the shell of the capsule and defining a chamber 28 between the shell and the sleeve. A pressure sensor 29 is operatively arranged to sense pressure within chamber 28 and communicates with the chamber through a fluid port 30 at one end of the shell of the capsule. As shown, the pressure sleeve 26 of capsule 20 extends from a point below the middle of the capsule up over the top end of the capsule.

On the opposite end of capsule 20 to pressure sensor 23 is pH sensor 22. In the preferred embodiment, pH sensor 22 is a conventional ISFET type pH sensor. ISFET stands for ion-selective field effect transistor and the sensor is derived from MOSFET technology (metal oxide screen field effect transistor). A current between a source and a drain is controlled by a gate voltage. The gate is composed of a special chemical layer which is sensitive to free hydrogen ions (pH). Versions of this layer have been developed using aluminum oxide, silicon nitride and titanium oxide. Free hydrogen ions influence the voltage between the gate and the source. The effect on the drain current is based solely on electrostatic effects, so the hydrogen ions do not need to migrate through the pH sensitive layer. This allows equilibrium, and thus pH measurement, to be achieved in a matter of seconds. The sensor is an entirely solid state sensor, unlike glass bulb sensors which require a bulb filled with buffer solution. Only the gate surface is exposed to the sample.

After activation and ingestion, capsule 20 senses and transmits measurements for at least 120 hours after activation. In the preferred embodiment, the range and accuracy of the sensors are generally 1 to 9.0 pH units with an accuracy of ±0.5 pH units, 0 to 350 mmHg with an accuracy of 5 mmHg, or 10% above 100 mmHg, and 25° to 49° C. with an accuracy of ±1° C.

In the preferred embodiment, the capsule transmits measurements at about 434 MHz and measures 26.8 mm long by 11.7 mm in diameter. As shown in FIG. 2, portable data receiver 17 worn by the subject receives and stores measurements transmitted by transmitter 16 in capsule 20. Data receiver 17 contains rechargeable batteries and when seated in a docking station allows for battery charging and data download. Data receiver includes an internal processor and a small display window 18. Data is downloaded from data receiver 17 through a docking station via a USB connection to computer 19. In this embodiment, computer 19 is a conventional Windows PC compatible laptop or desktop.

In the preferred embodiment, personal computer 19 includes a processor 31, data processing storage 34, a monitor or display 32, a user interface 33, and a printer 35. In the preferred embodiment, monitor 32 is a computer screen. However, monitor 32 may be any other device capable of providing an image or other data. In the preferred embodiment, user interface 33 includes a keyboard and a mouse. However, user input could be a touch-sensitive display device, a control panel or any other suitable device for interfacing with data processor 31.

The processing of the measurements from capsule 20 and the instructions for the user is generally provided using computer-executable instructions executed by a general-propose computer, such as a server or personal computer 19. However, it should be noted that this processing may be practiced with other computer system configurations, including internet appliances, hand-held devices, wearable computers, multi-processor systems, programmable consumer electronics, network PCs, mainframe computers and the like. The term computer or processor as used herein refers to any of the above devices as well as any other data processor. Some examples of processors are microprocessors, microcontrollers, CPUs, PICs, PLCs, PCs or microcomputers. A computer-readable medium comprises a medium configured to store or transport computer readable code, or in which computer readable code may be embedded. Some examples of computer-readable medium are CD-ROM disks, ROM cards, floppy disks, flash ROMS, RAM, nonvolatile ROM, magnetic tapes, computer hard drives, conventional hard disks, and servers on a network. The computer systems described above are for purposes of example only. An embodiment of the invention may be implemented in any type of computer system or programming or processing environment. In addition, it is meant to encompass processing that is performed in a distributed computing environment, were tasks or modules are performed by more than one processing device or by remote processing devices that are run through a communications network, such as a local area network, a wide area network or the internet. Thus, the term processor is to be interpreted expansively.

Processor 31 is programmed to interact with the user of system 15 and to guide the user in evaluating the gastrointestinal tract of a subject. Processor 31 provides step by step instructions to the user via monitor 32. With mouse the user clicks on images or links on monitor 32 in response to questions or instructions. Thus, the user proceeds through a series of screens. The user indicates that each task has been completed by clicking a "Next" button at the bottom of each screen. Only when this input is provided does the system allow the user to continue on to the next task or step, thereby helping assure that no critical step is missed in the process. The user can be a physician, a physician's assistant, a veterinarian, or anyone who is administering or testing a subject.

Figure 3:
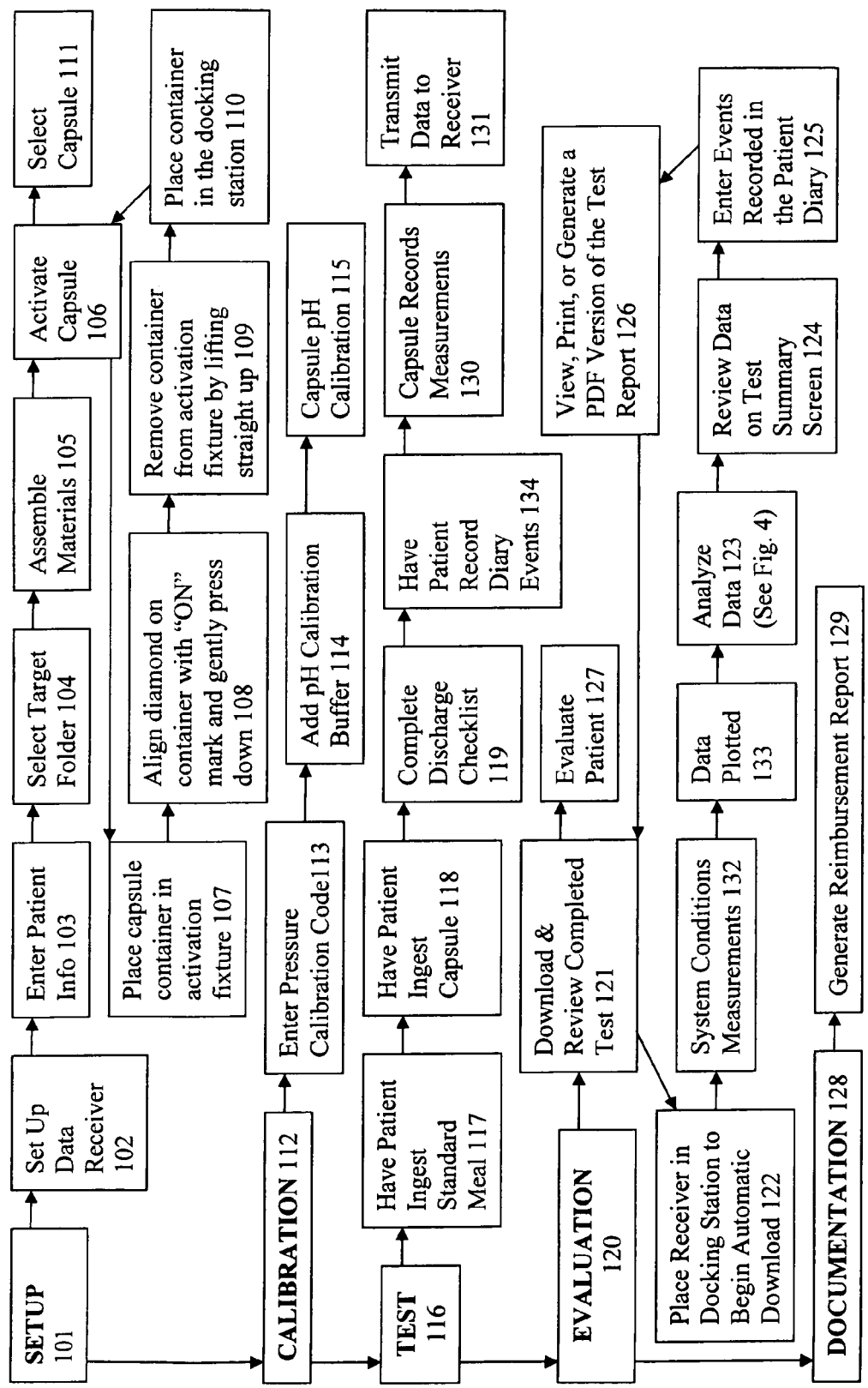
FIG. 3 is a flow chart of an embodiment of the improved method.
Figure 4A:
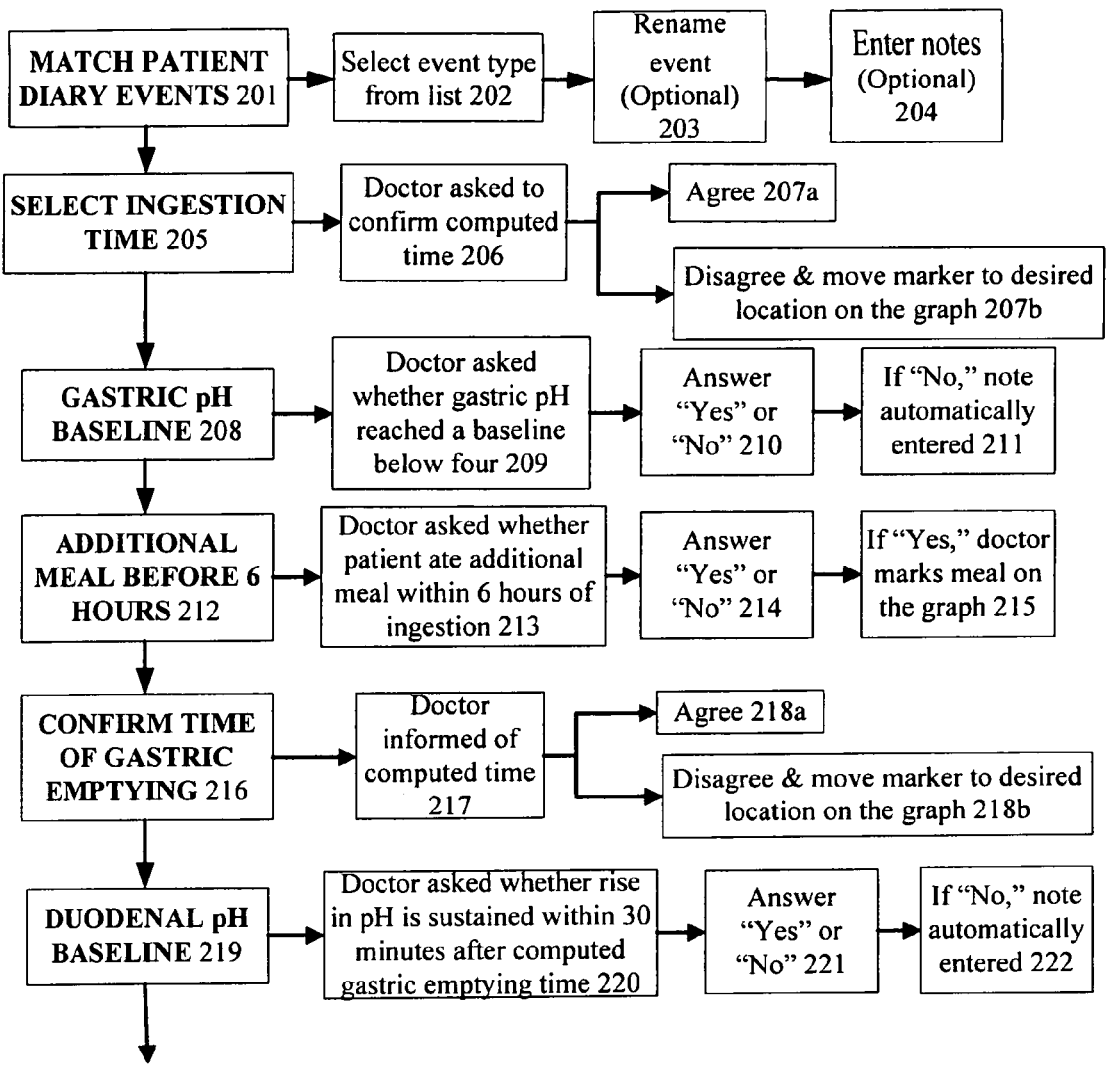
FIG. 4A and FIG. 4B are a flow chart of the data analysis step shown in FIG. 3.
Figure 4B:
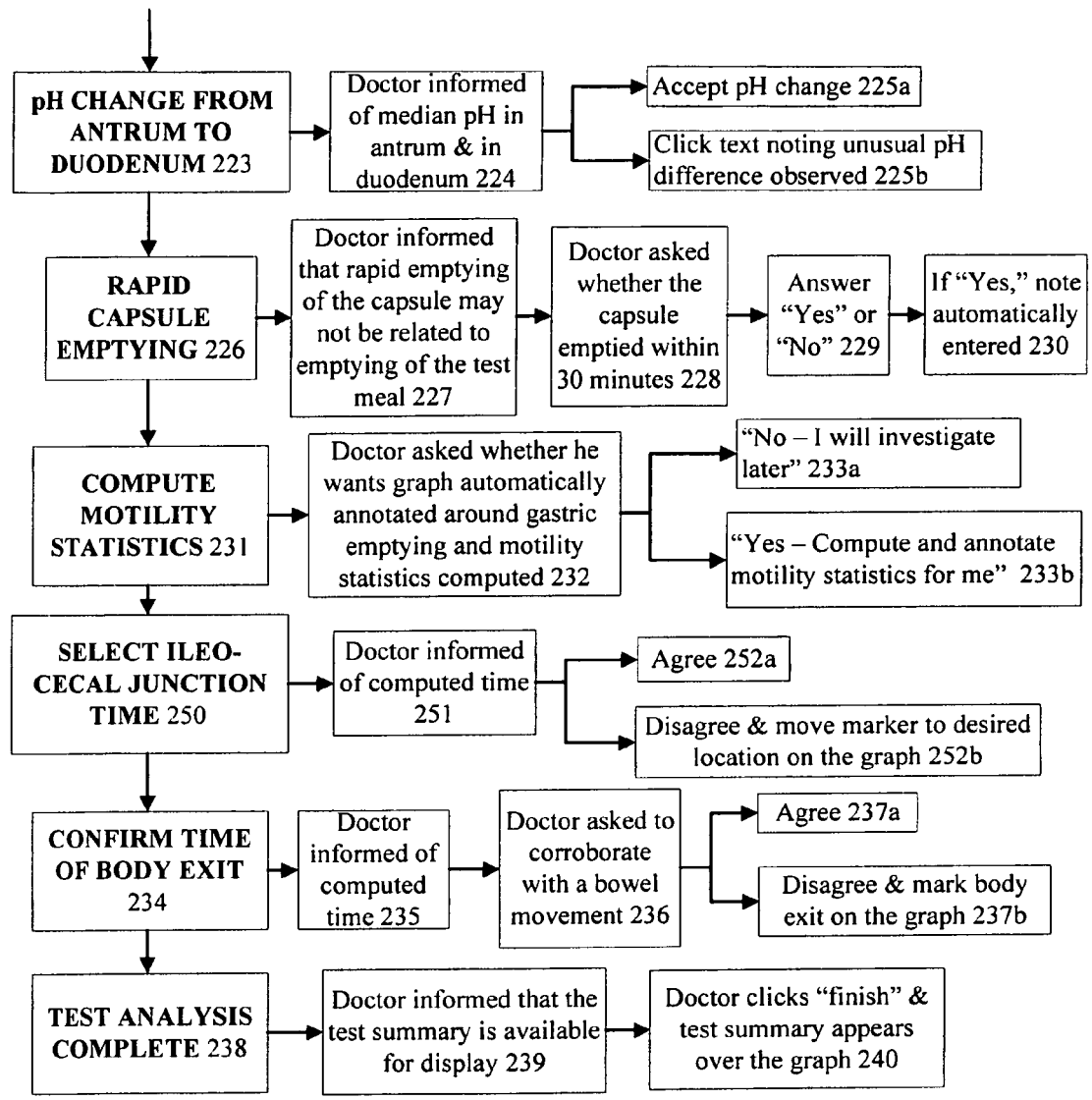
Figure 5:
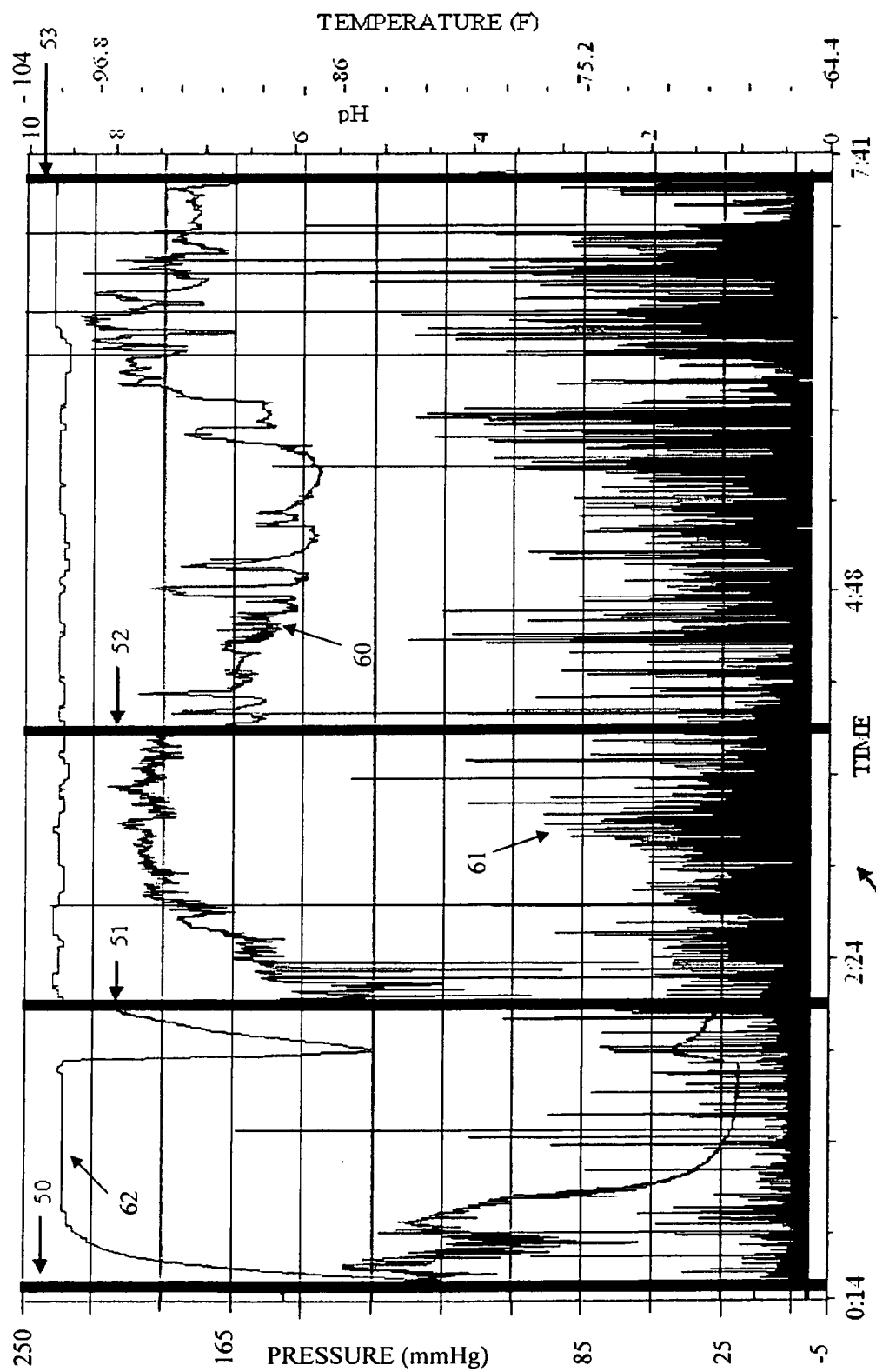
FIG. 5 is a graphical display of data with markers applied.

As shown in FIG. 3, the method of this embodiment includes a number of general phases, including a setup phase 101, a data receiver 102, a calibration phase 112, a testing phase 116, an evaluation phase 120, and a documentation phase 128.

In setup phase 101, data receiver 17 is first turned on by pressing an "Event" button on the receiver. A receiver docking station is connected to processor 31 via a USB port and data receiver 17 is placed in the docking station. An audio signal lets the user know that processor 31 has recognized the USB connection to the data receiver. The system then instructs the user to enter information 103 about the subject undergoing the test via user interface 33. These fields may include name, date of birth, gender, height, weight and user name. Required information, such as the name and date of birth of the subject, is marked with an asterisk. A "search for patient" button may be used to access existing records. In addition, certain contraindications for use are asked of the user, such as whether the subject has any implanted electromechanical devices, whether the subject has any GI obstructions, strictures or fistulas, whether the subject has a history of gastric bezoars, whether the subject has undergone GI surgery, whether the subject has difficulty swallowing, and whether the subject has Crohn's disease or diverticulosis. If one of these boxes is checked, a warning screen appears and the user may select to end the test or enter a justification for continuing and select to proceed. The "Next" button is not available until the user completes the contraindications step. Other questions that may be asked at this step include whether the subject is scheduled for an MRI in the following two weeks, whether the subject has taken motility medications, proton pump inhibitors, histamine2 blockers or antacids in the past 48 hours, whether the subject has had any abdominal surgery, whether the subject has any allergies, whether the subject is on any other medications, whether the subject is suffering with any medical symptoms, such as pain or constipation, and whether the subject smokes, is diabetic or pregnant.

Next, the user is prompted to select 104 a folder into which the test data is to be saved or stored. While the user may choose a folder to store the test records, a current default folder will be automatically selected, although the user may choose an alternative location.

The user is then instructed 105 to ensure that the necessary parts of system 15 are ready for use. These parts include a capsule activation fixture, capsule 20 and its container, and a buffer. Each item is illustrated on monitor 32, and the user must check off each item before the "Next" button becomes available.

The user is then instructed on how to activate 106 and select 111 capsule 20, and these instructions may include illustrations. The user is instructed to place capsule 20 in its container on the power activation fixture 107, to properly align the capsule with the fixtures "On" mark and to press down on the container and hold for five seconds 108. The user is then instructed to remove the container from the activation fixture 109 and to then place the capsule in the docking station well.

The user is then informed that the system is scanning for activated capsules. The serial number, signal strength and used status of capsules within range of the receiver are then displayed to the user. The user is asked to select from the screen the capsule matching the serial code on the container. A capsule having the status of "used" may not be selected.

Only when a capsule with a "not used" status is selected does the "Next" button become available to the user. The time and the non-calibrated pressure and pH data for the selected capsule are then displayed.

The user is then directed 112 to calibrate pressure sensor 23 and pH sensor 22. The user is directed 113 to enter a pressure calibration code found on the lid of the capsule container and the location of that code is shown. The user is then instructed with step by step illustrations to remove the lid of the container, to pour a pH calibration buffer into the capsule container 114, to remove the capsule from its seat by gently rocking it from side to side, and to then reinsert it into the container, with the pH sensor 110 degrees clockwise to the diamond-shaped window of the container. The capsule then automatically calibrates 115. The calibration is complete when the capsule pH reading remains stable at 6.0, and the message screen will change from "calibrating capsule" to "pH calibration complete". Also, a status bar will change from red to green. The "test in progress" icon will then appear in the status bar.

Capsule 20 is then used in testing phase 116 to measure parameters of the gastrointestinal tract of the subject. The user is directed to undock data receiver 17 and to position it on the subject using a lanyard or belt clip. The user is then instructed 117 to have the subject ingest a meal. In this embodiment a standard meal of an egg substitute, two slices of bread and water is ingested. Immediately after the subject finishes eating, the user is instructed to remove the capsule from the buffer, to rinse it in water, and to have the subject ingest the capsule 118 with a half cup of water. The user is then asked to verify that the receiver and capsule are communicating by observing a solid black block to the right of the pH value on the display.

A discharge checklist 119 is then provided to the user and the user is instructed to check each instruction to the subject after it is given. The checklist includes the user reviewing the patient instruction sheet with the subject, reviewing the patient diary usage with the subject, scheduling a date for data receiver return, and providing the subject with physician/office contact information in case of emergencies and questions. The box next to each task on the discharge checklist 119 must be checked before the user is able to click the "Finish" button.

As the capsule passes through the gastrointestinal tract of the subject, pH sensor 22 and pressure sensor 23 take measurements 130 and capsule 20 transmits 131 the measurements to receiver 17 being worn by the subject. The measurements are stored in receiver 17. In addition, an event button on receiver 17 allows the subject to electronically record a diary event 134, described further below, and to include a brief description of the event.

Once the receiver has been returned by the subject, the data is evaluated 120. When the subject has passed the capsule and returned receiver 17 to the user, the user docks it in the docking station and the system automatically detects that there is data on the receiver 122 and displays a message asking if the user wishes to open the subject's previously created test file stored on computer 31. Once the subject's test file is open, the user is prompted to select "Download Data" and the download screen appears.

Once the download is completed, the system conditions the downloaded measurements 132. In this embodiment, the pressure data from the subject is conditioned to distinguish real contraction data from artifacts or "noise" within the data set, as well as to discount physiologically improbable values. In the preferred embodiment, both concerns are addressed as part of a process which inspects each data value in the pressure measurement data set provided by the capsule. Because the conditioning utilizes constant minimum and maximum threshold values to determine and eliminate data spikes and artifacts, the input pressure data is baseline compensated. As mentioned above, the pressure data is then conditioned by filtering out those sets of data points or contractions whose peaks are above a predetermined threshold or limit. In the preferred embodiment, this threshold is about 200 mmHg. In addition, those contraction patterns whose peaks are less than a predetermined threshold or limit are also filtered out. In the preferred embodiment, this minimum threshold is about 9 mmHg. Thus, in the preferred embodiment the process considers a set of baseline compensated pressure measurements and begins evaluating each value in linear sequence from beginning to end. If a point is found to exceed the defined maximum, then the high value or spike is removed with its associated ascending and descending artifact values by traversing the data set both behind and ahead of the detected spike and zeroing the spike and any associated values, until either its termination or a new contraction is detected. The determination that an artifact has terminated is defined as any data point below a minimum pressure value. Contrarily, finding the next contraction from the high value is based on the detection of three consecutive ascending values, which is interpreted as an ascent in pressure, indicating the edge of a different contraction. Thus, in determining, for example, the area under the curve for a given time interval, a pressure point is included in the calculation only if its value is greater than or equal to the sum of the baseline pressure and the minimum threshold and is below the sum of the baseline pressure and the maximum threshold.

The conditioned data is then plotted 133 in graphical form 40 on screen 32 with a "Test Summary" overlay window. The software allows the user to selectively display pH versus time 60, pressure versus time 61 and temperature versus time 62 on the graph 40. The user may display these graphs separately or all three may be displayed in any combination or all together on the same graph. The user can also select to see just data from a specific region of the gastrointestinal tract of the subject.

The system then guides the user through a step-by-step analysis of the recorded data 123. The interactive analysis of the data includes a number of general steps, including matching subject diary events to the data 201, marking and confirming capsule ingestion 205, analyzing gastric pH baseline 208, identifying procedural violations such as the ingestion of an additional meal 212, marking and confirming gastric emptying 216, analyzing duodenal pH baseline 219, analyzing a pH change from the antrum to duodenum 223, determining rapid capsule emptying possibility 226, marking and confirming the ileo-cecal junction, marking and confirming body exit 234, and providing a complete test analysis 238, including segment transit times. To navigate through the program the user uses a "Go to previous" and "Go to next" button. A "Help" icon is available to assist the user with additional information on the step being viewed. As further described below, at the end the user may review the user's analysis of the test by clicking a "Finish" button and displaying a test summary.

The system first instructs 201 the user to match diary events recorded by the subject with the data recorded by capsule 20. At the beginning of the test the subject is directed to hit the event button on receiver 17 and record in a diary any events that may effect the data, such as the subject ingesting the capsule, the subject ingesting food, the subject ingesting a liquid, the subject experiencing abdominal pain or cramping, the subject experiencing nausea, the subject experiencing bloating or gas, the subject exercising or moving actively, the subject vomiting, the subject experiencing a bowel movement, the subject resting, and the subject waking up. A drop down menu of typical events is available to the user. The specific times that the event button on receiver 17 was pressed by the user are listed on the screen and the user is directed to select an event type from the menu 202 for each event. The user may also edit that description 203 if desired to more closely match it to the subject's written entries in the diary. The user may also enter notes 204 if desired. Annotating the graph with information from the subject's diary may help facilitate data analysis and interpretation. Thus, the user is allowed to select common events from the event icon drop down list or type in the user's own event caption and notes.

System 15 instructs the user in marking and confirming on graph 40 a number of transitional events for the capsule as it passed through the gastrointestinal tract. These events include ingestion of the capsule or the ingestion event time (IET), the capsule emptying from the stomach or the gastric emptying time (GET), the capsule entering the colon or passing the ileo-caecal junction (ICJ), and the capsule exiting the body or body exit time (BET). These times and their confirmation then allow the program to calculate transit time through different portions of the gastrointestinal tract of the subject, including gastric emptying time, small bowel transit time, colonic transit time, whole gut transit time and oral caecal transit time. The program identifies the stomach region of the subjects gastrointestinal tract as the span of data between entry of the capsule into the stomach, and the emptying of the capsule into the bowels. The program identifies the antrum region of the gastrointestinal tract as the span of data starting half an hour before gastric emptying to the gastric emptying event. The program identifies the duodenal region of the gastrointestinal tract as the span of data starting from gastric emptying to one half hour after gastric emptying. The small and large bowel region of the gastrointestinal tract are identified as being the span of data between gastric emptying and capsule body exit, differentiated by passage through the ICJ.

The first marker applied indicates the time the subject ingested the capsule or the IET. The user is instructed to confirm the time of capsule ingestion 205. System 15 performs its own computation for the IET and provides this information to the user 206 by placing a suggested marker 50 on graph 40. The information may also be provided by showing the coordinates. The user is then provided the option of agreeing and confirming 207a the suggested IET, or the user may disagree and move the marker to a different location 207b on graph 40.

The computed IET characterizes the ingestion event as two distinct event points: the point in time at which the capsule is swallowed by the subject, and the point in time in which the capsule enters the stomach. This distinction is made for the purpose of computational accuracy. The first point is used to track the beginning and duration of the test itself relative to the activation of the capsule and the physical act of being swallowed, whereas the second is used in conjunction with the algorithm which analysis the values for pH, temperature and pressure. Both points are found and used, but are maintained and referenced differently. The typical pH profile for the beginning of the test is characterized by the calibration phase, followed by a period of exposure to air, and concluded by a gastric phase. The calibration period is defined as the beginning of the test when pH values are at 6.0. When the capsule is exposed to air, the pH value will typically show a rapid increase to values well above 14. The gastric phase is identified by a sustained drop in pH values to well below the calibration value, generally between 1.0 and 4.0. The system first determines the average temperature across an entire test to establish baseline body temperature. The point within the temperature data set at or above the average is found, and the corresponding pH data point is found and used throughout the remainder of the program as a potential capsule stomach entry point. The program then proceeds to search the pH data set below the first value in the pH value set and this potential stomach entry point to locate a maximum pH value. The maximum value is then used as a boundary point. The pH minimum located between the beginning of the data set and the maximum point is defined as the physical swallow of the capsule. The pH minimum located between the potential stomach entry point and the pH maximum point becomes the final stomach entry point.

The user is then asked to analyze the gastric pH baseline 208. A baseline below 4 indicates normal acidic conditions and a baseline above 4 may need further characterization. The user is asked 209 whether gastric pH reached a baseline below 4. If the user response 210 is "No", a default annotation is inserted 211 into the "Notes" box indicating that a stomach pH below 4 was not observed. This annotation may be edited or comments and observations added by the user by typing in the "Notes" box. If the user answers "Yes", the user is instructed to proceed to the next step.

The user is then asked about any procedural deviations, particularly whether the subject had any additional meals within 6 hours of ingestion 212. The subject eating additional meals before 6 hours has elapsed can affect the validity of the test result. An additional meal is defined as anything other than limited quantities of water. Since snacks or meals should be recorded in the patient diary with an event notation, this information is used to provide analysis 212. The user is asked 213 to check the event history and whether the subject ate an additional meal within 6 hours of ingestion. If the user responds 214 "Yes", a corresponding marker is indicated 215 on graph 40. In this embodiment, the user is asked to insert this meal marker with a point annotation on graph 40. The program also reminds the user that the additional meal would not include the standard meal at the start of the test. If more than one additional meal is indicated, additional markers may be used to identify the time of each meal on graph 40.

Next, the user is instructed to confirm the time of gastric emptying 216. System 15 performs its own computation for GET and provides this information to the user 217 by placing a suggested marker 51 on graph 40. The information may also be provided by showing the coordinates. The user is then provided the option of agreeing and confirming 218a the suggested GET, or the user may disagree and move the marker to a different location 218b on graph 40.

The gastric emptying time is the elapsed time between ingestion of the capsule and the start of a sustained pH rise. The pH profile of gastric emptying is typically characterized by a sharp rise in pH from very low values, followed by a slight drop, and concluded by a substained pH at around neutral value. This corresponds with the exit of the capsule from the highly acidic environment of the stomach into the small bowel, where pH is at a neutral level for healthy subjects. The sustained pH rise typically will have no transient drops longer than ten minutes that exceed 50% of the pH change observed during the pH rise. To compute GET, the program looks at the data collected in reverse, starting at the end of the test and working towards the beginning of the test. The software detects gastric emptying by first filtering the pH profile to exclude predefined, physiologically improbably values and adjusting the raw data against the test's maximum and minimum to provide a more uniform trend, for the purpose of eliminating multiple artifact point that may result in a false reading. After filtration, the pH data set is traversed backwards to locate the demarcation between the sustained pH values of the bowel area and the small spike that immediately follows gastric emptying. After the stomach-bowel transition point is found, the data is then analyzed from the post-emptying spike to the next sustained low pH reading for a sharp sustained drop in the pH slope. The beginning point of the drop, with respect to the low (stomach) pH portion of the slope, is used as the point of gastric emptying and a suggested marker 51 is applied.

To assess the accuracy of GET, the pH data may be further analyzed with the user by looking closely at the duodenal pH baseline 219 and the pH change from the antrum to the duodenum 223. First, the user is asked 220 whether the rise in pH is sustained within 30 minutes after the indicated 51 GET. If the user selects 221 "No", a note is automatically entered 222 on graph 40 indicating that the duodenal pH baseline was not observed. If the user answers "Yes", the user is instructed to proceed to the next step.

The pH change from the antrum to the duodenum is then analyzed 223. The pH baseline 30 minutes before emptying is shown to the user, the pH baseline 30 minutes after emptying is shown to the user 224, and the user is shown the median pH in the antrum and the duodenum 224. The user is also instructed that typically a pH rise of 3 should be observed between the two. The user is requested to accept the pH change 225a and proceed to the next step or to select to have a note automatically inserted 225b on graph 40 indicating that an unusual pH difference was observed.

The user is then requested to indicate whether a rapid capsule emptying appears to have occurred 226. The user is informed that rapid emptying of the capsule may be related to emptying of the test meal 227. Based on the selected IET and GET, the program calculates the duration of gastric emptying. Typically, a preliminary cutoff for a normal subject is 4 hours and the minimum cutoff for a valid test is 30 minutes. The user is asked 228 whether they observed an unexpected rapid emptying, or emptying occurring within 30 minutes of IET. If the user responds 229 "Yes", a note is automatically entered 230 on graph 40. In an alternative embodiment, the user is also asked whether the user observes an unexpectedly slow emptying, typically emptying occurring outside 6 hours. Again, if the user responds "Yes", a note to that effect is automatically shown on graph 40. This annotation may be supplemented with comments or edited by the user.

Based on the answers provided by the user and the position of markers 50 and 51 on graph 40, statistics for pressure and pH for 30 minutes prior to GET and 30 minutes after GET are calculated. The user is provided with a query as to whether the user wishes to automatically annotate graph 40 with respect to gastric emptying and to compute the motility statistics 232. If the response 233a is "No", the user proceeds to the next step. If the response 233b is "Yes", the motility statistics are computed and provided on display for view to the user. In the preferred embodiment, for 30 minutes prior to GET the median pH is shown together with a minimum pH for the 30 minute time period and a maximum pH. In addition, the mean pressure is shown together with the maximum pressure. Motility index is also shown. The same information and calculations are shown on display screen 32 for the 30 minutes after the marked GET. U.S. Patent Publication No. 2008/0064938, entitled "Method of Determining Location of an Ingested Capsule", the entire contents of which are incorporated herein my reference, discloses the computation of motility index.

Next, the user is instructed to mark and confirm the ICJ time 250. System 15 performs its own computation for the ICJ and provides this information to the user 251 by placing a suggested marker 52 on graph 40. The information may also be provided by showing the coordinates. The user is then provided the option of agreeing and confirming 252a the suggested ICJ time, or the user may disagree and move the marker to a different location 252b on graph 40.

In this embodiment, a combined change in pH and motility index is used by the program to mark 52 the transition between the distal ileum and the caecum. A change in pH and a change in either frequency of contractions or motility index that correlates with variations in a template are used to compute the suggested ICJ 52, as further described in U.S. Patent Publication No. 2008/0064938, entitled "Method of Determining Location of an Ingested Capsule", the entire contents of which are incorporated herein my reference.

With respect to both GET and ICJ, the program may also prompt the user to comment on any notable pressure characteristics around the event time. These comments may also be displayed on graph 40 or included in the test summary if desired by the user.

Based on the selected GET and ICJ, the program calculates the small bowel transit time (SBTT). A standard SBTT is shown to the user and the user is asked whether they observed an unexpected rapid or slow transit. If the user responds "Yes", a note is automatically entered on graph 40. This annotation may be supplemented with comments or edited by the user.

Next, the user is instructed to mark and confirm the body exit time (BET) 234. System 15 performs its own computation for BET and provides this information to the user 235 by placing a suggested marker 53 on graph 40. The information may also be provided by showing the coordinates. The user is then asked to refer to the event markers and any indicated bowel movement event marker to corroborate the BET 236. The user is then provided the option of agreeing and confirming 237a the suggested BET, or the user may disagree and move the marker to a different location 237b on graph 40.

In this embodiment, BET is computed from a set of data trends as the capsule exits the body and is exposed to a non-physiological environment. A typical graph will show the pressure decreases to near zero or its calibrated offset and temperature drops sharply. The program uses temperature to determine BET. The system first determines a range of temperatures which represent body temperature using a pre-defined temperature of 32° C. as a minimum threshold. The temperature data set is then inspected in reverse chronological order from the end of the test to locate the first data point which lies within the determined body temperature range and this is used. In the worst case scenario, where the temperature cannot be characterized, the pressure data set is analyzed in backwards chronological order for the first sharp rise in pressure values. The time of the detected pressure rise is then defined by the algorithm as the BET.

Based on the selected ICJ and BET, the program calculates the colonic transit time (CTT). A standard CTT is shown to the user and the user is asked whether they observed an unexpected rapid or slow transit. If the user responds "Yes", a note is automatically entered on graph 40. This annotation may be supplemented with comments or edited by the user.

Whole gut transit time or total transit time (TTT) is the time from capsule ingestion to body exit and this may also be provided to the user for analysis in comparison to a standard.

In this embodiment, system 15 will also provide the user with a number of warnings or alerts during the process. If gastric emptying occurs within 30 minutes of capsule ingestion, a warning is provided to the user indicating that the test results are probably not valid. If a pH change of less than 3 units is indicated from the antrum to the duodenum, then the program provides the user with a warning that further clarification may be needed. If low voltage is detected in capsule 20, an alert is provided to the user. This alert advises the user to disregard or question all data collected after the start of the alert as the temperature readings may be artificially low.

Once BET has been confirmed 234, the test analysis is completed 238. The user is informed that a test summary is available for display 239. The user is also given the chance to further edit any notes or annotations entered on graph 40. The user may then elect to finish the analysis, in which case the test summary appears 240 over graph 40. The test summary displays the subject transit times based on the user confirmed placement of markers 50-53. In this embodiment, the test summary will also show the system computed transit times together with information regarding the transit times for a standard or healthy subject with respect to the indicated regions. In this embodiment, gastric emptying time GET is shown and a standard of about 4 hours and under is indicated. Small bowel transit time SBTT, colonic transit time CTT and whole gut transit time TTT are also shown. It is contemplated that other transit times may be shown, such as oral-caecal transit time (ingestion to the ICJ event).

After a completed test has been downloaded and reviewed 121, the summary sheet may be reviewed by the user 124 on monitor 32. In addition, events recorded in the patient diary may be entered 125 on the summary sheet. The user may then generate a PDF version of the summary sheet or print the summary sheet 126 on printer 35. The information may be used to evaluate and diagnose the user 127. Finally, the user may generate billing or file documentation 128, including a reimbursement report 129 that is printable on printer 35.

While this embodiment has been described in relation to the gastrointestinal tract of a human, it is contemplated that the system may be used in connection with the gastrointestinal tract of other animals.

The present invention contemplates that many changes and modifications may be made. Therefore, while the presently-preferred form of the improved method and system have been shown and described, and a number of alternatives discussed, persons skilled in this art will readily appreciate that various additional changes and modifications may be made without departing from the spirit of the invention, as defined and differentiated by the following claims.

What is claimed is:

1. A method for determining a capsule transit time in the gastrointestinal tract comprising:
   recording sensor measurements from an ingested capsule comprising at least one sensor, wherein said at least one sensor is selected from a pH sensor, a pressure sensor and a temperature sensor, as said capsule passes through said gastrointestinal tract, wherein said sensor measurements are related to a parameter of said gastrointestinal tract;
   transmitting said measurements to a processor, and using said processor to:
      condition said sensor measurements to provide sensor data, the sensor data including at least a pH data, a pressure data and/or a temperature data;
      establish a baseline body temperature by determining an average body temperature of the temperature data;
      define a physical swallow of the capsule as a pH minimum located between a beginning of the pH data and a boundary point, the boundary point being a maximum pH value located in pH data after a potential stomach entry point, the potential stomach entry point being a pH data point corresponding to a temperature data point at or above the baseline body temperature;
      plot said sensor data on a display as a function of time to produce a plot representing the gastrointestinal tract parameter;
      provide a suggested marker on said plot at a location identifying a gastrointestinal transition time;
      receive input from a user in response to a query regarding the location of the suggested marker on said plot;
      set the suggested marker on said plot at a location as a function of said input; and
      determine a capsule transit time in said gastrointestinal tract as a function of the location of said suggested marker as set on said plot.

2. The method set forth in claim 1, wherein said step of transmitting said sensor measurements to a processor comprises steps of: transmitting said sensor measurements from said capsule to a receiver; and downloading said sensor measurements from said receiver to said processor.

3. The method set forth in claim 1, wherein said step of conditioning said measurements to provide sensor data comprises steps of screening said sensor measurements to verify they are valid.

4. The method set forth in claim 1, wherein said plot is a graph.

5. The method set forth in claim 1, wherein said step of providing a suggested marker comprises steps seeking confirmation from said user that said suggested marker is at a desired location.

6. The method set forth in claim 5, wherein said input comprises confirmation by said user that said suggested marker is at said desired location.

7. The method set forth in claim 1, wherein said step of providing a suggested marker comprises steps prompting said user to move said suggested marker by way of an input device communicating with said processor.

8. The method set forth in claim 7, wherein said input comprises movement of said suggested marker by said user with said input device.

9. The method set forth in claim 1, wherein said step of providing a suggested marker comprises a step of prompting said user to position said suggested marker at desired location on said plot with an input device communicating with said processor.

10. The method set forth in claim 9, wherein said input comprises placement of said suggested marker by said user with said input device.

11. The method set forth in claim 1, wherein said sensor data is shown in a first color on said plot and said suggested marker is shown on said plot in a second color different from said first color.

12. The method set forth in claim 1, wherein said location of said suggested marker on said plot corresponds to a gastrointestinal event selected from a group consisting of ingestion, gastric emptying, colonic entry, and body exit.

13. The method set forth in claim 1, wherein said transit time is selected from a group consisting of gastric emptying time, small bowel transit time, colonic transit time, whole gut transit time, and oral caecal transit time.

14. The method set forth in claim 13, wherein said transit time is displayed on said display.

15. The method set forth in claim 1, and further comprising a step of using said processor to compare said transit time to a standard transit time.

16. The method set forth in claim 15, wherein a result of said compare step is displayed on said display.

17. The method set forth in claim 1, and further comprising a step of using said processor to compare said sensor data to a standard.

18. The method set forth in claim 17, wherein said standard is selected from a group consisting of stomach pH, pH rise from stomach to small bowel, pressure in a portion of said gastrointestinal tract, and a temperature fluctuation.

19. The method set forth in claim 1, and further comprising steps of: using a receiver to record an event associated with said subject during transit of said capsule; using said processor to correlate said event with said sensor data; and using said processor to notate said event on said plot.

20. The method set forth in claim 19, wherein said event is selected from a group consisting of said subject ingesting said capsule, ingesting food, ingesting liquid, experiencing pain, experiencing nausea, experiencing gas, experiencing bloating, exercising, moving actively, vomiting, resting, waking up, and experiencing a bowel movement.

21. The method set forth in claim 1, and further comprising a step of using said processor to receive a notation or comments associated with said plot.

22. The method set forth in claim 1, further comprising using said processor to define a final stomach entry point as a pH minimum located between the potential stomach entry point and the boundary point.

23. The method set forth in claim 1, further comprising using said processor to filter the pH data.

24. The method set forth in claim 23, further comprising using said processor to detect gastric emptying, wherein, after filtering the pH data:
  detect a stomach-bowel transition point by traversing a pH data set from an end of the pH data to a beginning of the pH data to locate a demarcation between sustained pH values of a bowel area and a spike that immediately follows gastric emptying;
  analyze the pH data from a post-emptying spike to a next sustained low pH reading for sustained drop in pH slope;
  use a beginning point of the sustained drop as a point of gastric emptying; and
  wherein said provide a suggested marker on said plot at a location includes providing said suggested marker at the point of gastric emptying.

25. A non-transitory computer-readable medium encoded with computer-executable instructions for performing a method comprising:
  receiving measurements related to a gastrointestinal tract parameter of a subject recorded by at least one sensor, wherein said sensor is selected from a pH sensor, a pressure sensor and a temperature sensor, on a capsule ingested by said subject;
  conditioning said measurements to provide sensor data, the sensor data including at least a pH data, a pressure data and/or a temperature data;
  establishing a baseline body temperature by determining an average body temperature of the temperature data;
  defining a physical swallow of the capsule as a pH minimum located between a beginning of the pH data and a boundary point, the boundary point being a maximum pH value located in pH data after a potential stomach entry point, the potential stomach entry point being a pH data point corresponding to a temperature data point at or above the baseline body temperature;
  plotting said sensor data on a display as a function of time to produce a plot representing the gastrointestinal tract parameter;
  providing a suggested marker on said plot at a location identifying a gastrointestinal transition time;
  receiving, via an input device, input from a user in response to a query regarding the location of the suggested marker on said plot;
  setting the suggested marker on said plot at a location as a function of said input; and
  determining a capsule transit time in said gastrointestinal tract as a function of the location of said suggested marker as set on said plot.

26. The non-transitory computer readable medium set forth in claim 25, wherein said condition said measurements to provide sensor data comprises screening said measurements to verify that they are valid.

27. The non-transitory computer readable medium set forth in claim 25, wherein said plot is a graph.

28. The non-transitory computer readable medium set forth in claim 25, wherein said providing a suggested marker compresses seeking confirmation from said user that said suggested marker is at a desired location.

29. The non-transitory computer readable medium set forth in claim 28, wherein said input comprises confirmation by said user that said suggested marker is at said desired location.

30. The non-transitory computer readable medium set forth in claim 25, wherein said input comprises movement of said suggested marker by said user with said input device.

31. The non-transitory computer readable medium set forth in claim 25, wherein said providing a suggested marker comprises prompting said user to position the suggested marker at a desired location on said plot with said input device.

32. The non-transitory computer readable medium set forth in claim 25, wherein said sensor data is shown in a first color on said plot and said marker is shown on said plot in a second color different from said first color.

33. The non-transitory computer readable medium set forth in claim 25, wherein said location of said marker on said plot corresponds to a gastrointestinal event selected from a group consisting of ingestion, gastric emptying, colonic entry, and body exit.

34. The non-transitory computer readable medium set forth in claim 25, wherein said transit time is selected from a group consisting of gastric emptying time, small bowel transit time, colonic transit time, whole gut transit time, and oral caecal transit time.

35. The non-transitory computer readable medium set forth in claim 34, wherein said transit time is displayed on said display.

36. The non-transitory computer readable medium set forth in claim 25, and further comprising comparing said transit time to a standard transit time.

37. The non-transitory computer readable medium set forth in claim 36, wherein a result of said comparison is displayed on said display.

38. The non-transitory computer readable medium set forth in claim 25, and further comprising comparing said sensor data to a standard.

39. The non-transitory computer readable medium set forth in claim 38, wherein said standard is selected from a group consisting of stomach pH, pH rise from stomach to small bowel, pressure in a portion of said gastrointestinal tract, and a temperature fluctuation.

40. The non-transitory computer readable medium set forth in claim 25, and further comprising receiving a recorded event associated with said subject during transit of said capsule via a receiver, correlating said event with said sensor data; and notating said event on said plot.

41. The non-transitory computer readable medium set forth in claim 40, wherein said event is selected from a group consisting of said subject ingesting said capsule, ingesting food, ingesting liquid, experiencing pain, experiencing nausea, experiencing gas, experiencing bloating, exercising, moving actively, vomiting, resting, waking up, and experiencing a bowel movement.

42. The non-transitory computer readable medium set forth in claim 25, and further comprising entering a notation or comments associated with said plot.

43. The non-transitory computer readable medium set forth in claim 25, wherein the computer-executable instructions further comprise defining a final stomach entry point as a pH minimum located between the potential stomach entry point and the boundary point.

44. The non-transitory computer readable medium set forth in claim 25, wherein the computer executable instructions further comprise filtering the pH data.

45. The non-transitory computer readable medium set forth in claim 44, wherein the computer-executable instructions further comprise detecting gastric emptying, after filtering the pH data, by:
    detecting a stomach-bowel transition point by traversing a pH data set from an end of the pH data to a beginning of the pH data to locate a demarcation between sustained pH values of a bowel area and a spike that immediately follows gastric emptying;
    analyzing the pH data from a post-emptying spike to a next sustained low pH reading for a sustained drop in pH slope; and
    using a beginning point of the sustained drop as a point of gastric emptying;
    wherein said providing a suggested marker on said plot at a location includes providing said suggested marker at the point of gastric emptying.

46. A system for analyzing measurements obtained from the gastrointestinal tract of a subject comprising:
    an ingestible capsule having at least one sensor, wherein said at least one sensor is selected from a pH sensor, a pressure sensor and a temperature sensor, for recording measurements as said capsule passes through at least a portion of said subject's gastrointestinal tract, said measurements are related to a parameter of the gastrointestinal tract;
    a receiver adapted to receive said measurements when transmitted from said capsule;
    a processor adapted to communicate with said receiver;
    a display in communication with said processor;
    an input device in communication with said processor;
    said processor programmed to:
        receive said measurements;
        condition said measurements to provide sensor data, the sensor data including at least a pH data, a pressure data and/or a temperature data;
        establish a baseline body temperature by determining an average body temperature of the temperature data;
        define a physical swallow of the capsule as a pH minimum located between a beginning of the pH data and a boundary point, the boundary point being a maximum pH value located in pH data after a potential stomach entry point, the potential stomach entry point being a pH data point corresponding to a temperature data point at or above the baseline body temperature;
        plot said sensor data on said display as a function of time to produce a plot representing the gastrointestinal tract parameter;
        provide a suggested marker on said plot at a location identifying a gastrointestinal transition time;
        receive input from said input device in response to a query regarding the location of the suggested marker on said plot;
        set the suggested marker on said plot at a location as a function of said input; and
        determine a capsule transit time in said gastrointestinal tract as a function of the location of said suggested marker as set on said plot.

47. The system set forth in claim 46, wherein said conditioning said measurements to provide sensor data comprises screening said measurements to verify that they are valid.

48. The system set forth in claim 46, wherein said plot is a graph.

49. The system set forth in claim 46, wherein said providing a suggested marker comprises seeking confirmation that said suggested marker is at a desired location.

50. The system set forth in claim 49, wherein said input comprises confirmation that said suggested marker is at said desired location.

51. The system set forth in claim 46, wherein said input comprises movement of said suggested marker with said input device.

52. The system set forth in claim 46, wherein said providing a suggested marker comprises allowing a user to position the suggested marker at a desired location on said plot with said input device.

53. The system set forth in claim 46, wherein said sensor data is shown in a first color on said plot and said marker is shown on said plot in a second color different from said first color.

54. The system set forth in claim 46, wherein said location of said suggested marker on said plot corresponds to a gastrointestinal event selected from a group consisting of ingestion gastric emptying, colonic entry, and body exit.

55. The system set forth in claim 46, wherein said transit time is selected from a group consisting of gastric emptying time, small bowel transit time, colonic transit time, whole gut transit time, and oral caecal transit time.

56. The system set forth in claim 55, wherein said processor is programmed to display said transit time on said display.

57. The system set forth in claim 46, wherein said processor is programmed to compare said transit time to a standard transit time.

58. The system set forth in claim 57, wherein said processor is programmed to display a result of said comparison on said display.

59. The system set forth in claim 46, wherein said processor is programmed to compare said sensor data to a standard.

60. The system set forth in claim 59, wherein said standard is selected from a group consisting of stomach pH, pH rise from stomach to small bowel, pressure in a portion of said gastrointestinal tract, and a temperature fluctuation.

61. The system set forth in claim 46, wherein said processor is programmed to: receive a recorded event associated with said subject during transit of said capsule via the receiver; correlate said event with said sensor data; and notate said event on said plot.

62. The system set forth in claim 61, wherein said event is selected from a group consisting of said subject ingesting said capsule, ingesting food, ingesting liquid, experiencing pain, experiencing nausea, experiencing gas, experiencing bloating, exercising, moving actively, vomiting, resting, waking up, and experiencing a bowel movement.

63. The system set forth in claim 46, wherein said processor is programmed to receive from said input device and display a notation or comment associated with said plot.

64. The system set forth in claim 46, wherein the processor is further configured to define a final stomach entry point as a pH minimum located between the potential stomach entry point and the boundary point.

65. The system set forth in claim 46, wherein the processor is further configured to filter the pH data.

66. The system set forth in claim 65, wherein the processor is further configured to detect gastric emptying, wherein, after filtering the pH data, the processor is further configured to:
- detect a stomach-bowel transition point by traversing a pH data set from an end of the pH data to a beginning of the pH data to locate a demarcation between sustained pH values of a bowel area and a spike that immediately follows gastric emptying;
- analyze the pH data from a post-emptying spike to a next sustained low pH reading for a sustained drop in pH slope; and
- use a beginning point of the sustained drop as a point of gastric emptying;
- wherein said provide a suggested marker on said plot at a location includes to provide said suggested marker at the point of gastric emptying.

* * * * *